(12) United States Patent
Müller-Hartmann et al.

(10) Patent No.: US 7,678,564 B2
(45) Date of Patent: Mar. 16, 2010

(54) CONTAINER WITH AT LEAST ONE ELECTRODE

(75) Inventors: Herbert Müller-Hartmann, Köln (DE); Michael Habig, Köln (DE); Peter Hoffmann, Köln (DE); Gregor Siebenkotten, Frechen-Königsdorf (DE)

(73) Assignee: Lonza Cologne AG (DE)

( * ) Notice: Subject to any disclaimer, the term of this patent is extended or adjusted under 35 U.S.C. 154(b) by 1361 days.

(21) Appl. No.: 10/505,149

(22) PCT Filed: Feb. 20, 2003

(86) PCT No.: PCT/DE03/00536

§ 371 (c)(1),
(2), (4) Date: Nov. 22, 2004

(87) PCT Pub. No.: WO03/070875

PCT Pub. Date: Aug. 28, 2003

(65) Prior Publication Data

US 2005/0064578 A1   Mar. 24, 2005

(30) Foreign Application Priority Data

Feb. 20, 2002  (DE) .................................. 102 08 188

(51) Int. Cl.
*C12M 1/42*    (2006.01)
*C12M 1/00*    (2006.01)
*B41J 2/01*    (2006.01)

(52) U.S. Cl. ..................... 435/285.2; 435/283.1; 347/1

(58) Field of Classification Search .............. 435/285.2, 435/283.1; 347/1
See application file for complete search history.

(56) References Cited

U.S. PATENT DOCUMENTS 4,761,541 A * 8/1988 Batliwalla et al. ........... 219/528

(Continued)

FOREIGN PATENT DOCUMENTS

DE       198 26 153 A1    12/1999

(Continued)

OTHER PUBLICATIONS

MedProbe Mar. 5, 2001, p. 1-3. From Internet Archive http://web.archive.org/web/20010503045345/http://www.medprobe.com/no/mbp.html.*

(Continued)

*Primary Examiner*—Walter D Griffin
*Assistant Examiner*—Lydia Edwards
(74) *Attorney, Agent, or Firm*—Joyce von Natzmer; Pequignot + Myers LLC

(57) ABSTRACT

The invention relates to a container 20, 30 for receiving an aqueous solution, which is formed at least partially by an outer limit 21 forming an inner chamber 22, 32 for receiving the solution, and which comprises at least one area which acts as an electrode 25, 26, 33, 34 when an electric voltage is applied and a subsequent discharge occurs, wherein at least one electrode 25, 26, 33, 34 is made of a conductive synthetic material at least based on a plastic material which is doped with at least one conductive substance. A container 20, 30 of the above-mentioned kind is created this way, which is simple and economical to produce and also, for example, enables an efficient transfection of living cells by means of electroporation or an effective electrofusion.

41 Claims, 17 Drawing Sheets a)        b)

U.S. PATENT DOCUMENTS

| | | | |
|---|---|---|---|
| 4,765,874 A * | 8/1988 | Modes et al. | 205/635 |
| 5,128,257 A * | 7/1992 | Baer | 435/173.6 |
| 5,183,744 A * | 2/1993 | Kawamura et al. | 435/30 |
| 5,468,918 A | 11/1995 | Kanno et al. | |
| 5,676,646 A * | 10/1997 | Hofmann et al. | 604/6.11 |
| 6,001,617 A | 12/1999 | Raptis | |
| 6,040,184 A | 3/2000 | Greener et al. | |
| 6,090,617 A * | 7/2000 | Meserol | 435/285.2 |
| 6,383,802 B1 * | 5/2002 | Bertling | 435/287.2 |
| 6,830,848 B1 * | 12/2004 | Fujiwara et al. | 429/213 |
| 7,101,703 B2 * | 9/2006 | Palermo | 435/285.2 |
| 2002/0005352 A1 * | 1/2002 | Offenbacher | 204/415 |
| 2002/0025573 A1 * | 2/2002 | Maher et al. | 435/287.1 |
| 2002/0028368 A1 * | 3/2002 | Saito et al. | 429/34 |
| 2002/0127467 A1 * | 9/2002 | Watanabe et al. | 429/90 |
| 2002/0164776 A1 | 11/2002 | Beichmann et al. | |

FOREIGN PATENT DOCUMENTS

| | | |
|---|---|---|
| DE | 199 42 347 A1 | 3/2001 |
| DE | 101 16 211 A1 | 10/2002 |
| EP | 0 402 554 A1 | 12/1990 |
| EP | 0 563 281 B1 | 8/1998 |
| EP | 0 588 906 A1 | 8/2002 |
| FR | 2 661 280 A1 | 10/1991 |
| JP | 0 6188 532 A | 7/1994 |
| JP | 11 103858 | 4/1999 |
| WO | WO 99/64157 * | 12/1999 |
| WO | WO01 70928 | 9/2001 |

OTHER PUBLICATIONS

Loomis-Husselbee et al, "Electroporation can cause artefacts due to solubilization of cations from the electrode plates. Aluminum ions enhance conversion of Inositol 1,3,4,5-tetrakisphosphate into inositol 1,4,5-trisphosphate in electroporated L1210 cells," Biochem J. 277 (3):883-5 (Aug. 1, 1991). (Full Article).

Stapulionis R., "Electric pulse-induced precipitation of biological macromolecules in electroporation," Bioelectrochem Bioenerg 48(1):249-54 (Feb. 1999). (Full Article).

Eurogentec, "Easyject Plus User's Manual Passage", pp. 1-27, 30-39 (Jul. 10, 1992).

Loomis-Husselbee et al, "Electroporation can cause artefacts due to solubilization of cations from the electrode plates. Aluminum ions enhance conversion of Inositol 1,3,4,5-tetrakisphosphate into inositol 1,4,5-trisphosphate in electroporated L1210 cells," Biochem J. 277 (3):883-5 (Aug. 1, 1991) (Abstract only).

Stapulionis R., "Electric pulse-induced precipitation of biological macromolecules in electroporation," Bioelectrochem Bioenerg 48(1):249-54 (Feb. 1999) (Abstract only).

* cited by examiner a) Aluminium/Solution A b) Aluminium/Solution B c) PC+CF+Gr/Solution A d) PC+CF+Gr /Solution B a)

b)

a)                  b)

a)                                            b)

a)  b)

a)

b)

a) b)

b)

a)

CONTAINER WITH AT LEAST ONE ELECTRODE

This is the U.S. national stage entry of PCT/DE03/00536, filed Feb. 20, 2003, designating the U.S., whose content is fully incorporated herein by reference.

FIELD OF THE INVENTION

The invention concerns a container for receiving an aqueous solution, and in particular cells, derivatives of cells, subcellular particles and/or vesicles, which is formed at least partially by an outer limit forming an inner chamber for receiving said solution, and which comprises at least one area which acts as an electrode when an electric voltage is applied and a subsequent discharge occurs.

BACKGROUND OF THE INVENTION

Transferring biologically active molecules, such as, for example, DNAs, RNAs or proteins, into living cells is an important tool for analysis of biological functions of these molecules. Electroporation is a preferred method for transferring foreign molecules into the cells, which in contrast to chemical methods causes less undesirable changes of the biological structure and function of the target cell. During electroporation the foreign molecules are introduced into the cells from an aqueous solution, preferably a buffer solution adapted to the cells or a cell culture medium, by a short-time current flow, i.e. the pulse of a discharging capacitor, whereby the cell membrane is made permeable for the foreign molecules by effect of the short electric pulses. Solution and cell suspension, respectively, are usually provided in a so-called cuvette, i.e. a small container which is open at the top and which comprises two oppositely and parallel arranged electrodes disposed in the sidewalls near the bottom and serving for the application of electric voltage. Through the temporarily emerging "pores" in the cell membrane the biologically active molecules initially reach the cytoplasm where they eventually already exert their function to be analysed. At certain conditions the molecules subsequently also enter the nucleus of the cell. Particularly with the introduction of DNA into animal cells, the so-called transfection, specific problems often arise during electroporation because of the fragility of the cells since the efficiency of transfection is affected by the survival rate of the cells as an important parameter.

Due to the temporarily applied intensive electric field, i.e. a short pulse with high current density, cells, derivatives of cells, subcellular particles and/or vesicles can also be fused. During this so-called electrofusion at first, for instance, the membranes of the cells are brought in close contact by an inhomogeneous alternating electric field. The subsequent application of an electric field pulse leads to an interaction of parts of the membranes, which finally leads to cell fusion. Comparable devices such as the ones used for electroporation can be used for electrofusion as well.

Containers as mentioned above are known and primarily used for electroporation or electrofusion in the form of cuvettes having inserted electrodes made of metal. Containers used for this purpose are mostly small vessels which are closed at the bottom and open at the top and whose inner space is build by two pairs of parallel and oppositely arranged sidewalls. The inner space serves for receiving of the cell suspension, i.e. usually an aqueous buffer solution or a cell culture medium, in which the cells to be treated are suspended. Such cuvettes mostly comprise a pair of electrodes for application of an electric voltage disposed near the bottom of a pair of oppositely arranged sidewalls. During an electric discharge an electric current flows through the cell suspension between both electrodes, which enables an introduction of nucleic acids or other molecules into the cells or, depending on the selected conditions, leads to fusion of cells. The electrodes are mostly made of metal, wherein aluminium is frequently used. But it is an disadvantage of these known, commercially available cuvettes that metal ions are emitted into the buffer solution during the electric discharge, which can cause an undesirable stimulation of the cells at lower concentrations or, at higher concentrations, act toxic on the cells. For instance, using cuvettes made of aluminium a negative effect due to the release of $Al^{3+}$ ions could be demonstrated (Loomis-Husselbee et al., Biochem J 1991, 277 (Pt 3), 883-885). Furthermore, using cuvettes having electrodes made of metal generation of undesirable precipitates may occur, which are also generated due to the release of metal ions from the electrodes. The precipitates may be metal hydroxides or complexes of metal ions with biological macromolecules of the buffer solution (Stapulionis, Bioelectrochem Bioenerg 1999, 48(1), 249-254). Finally, it is another disadvantage of cuvettes made of aluminium that the resistance of the cuvettes decreases during discharge, presumably because a layer of oxidized aluminium having a higher resistance is released from the electrode by the current flow. Additionally, cuvettes having electrodes made of metal are difficult to produce and very expensive.

U.S. Pat. No. 6,001,617 discloses a device for cultivation of cells, which can be used for electroporation as well as for electrofusion of cells. The device consists of a round container having an optically transparent bottom on which a layer of cells can adhere and grow. The bottom of the container may consist of an optically transparent, non-conductive material being coated with an electrically conductive material, or can be completely made of an optically transparent and electroconductive material. The electroconductive bottom is contacted via a band-like electrode made of metal and being circumferentially disposed in the wall area. To act as counter electrode a likewise circular band is provided. It is one drawback of this known device that it is primarily provided and suitable for electroporation of adhering cells. Using this device for transfection of suspended cells is limited and merely possible if low efficiency is accepted. Due to the ring-like circular contacting of the bottom electrode and the counter electrode being likewise circumferentially disposed in the wall area a homogenous electric field cannot be generated so that equal transfection of all cells cannot be achieved. This effect is increased by the fact that the intrinsically conductive plastics used have a higher resistance as they are provided as thin coating. Thus, the cells adhering to the bottom in the centre of the surface can only be transfected with very low efficiency. Furthermore, because of the sophisticated construction and the fact that the intrinsically conductive plastics used are not mouldable, the production of the known container is very expensive.

SUMMARY OF THE INVENTION

It is thus the object of the invention to create a container as mentioned above in order to overcome the existing deficiencies, which can be produced easily and cost-effectively, and which allows an efficient treatment of cells, derivatives of cells, subcellular particles and/or vesicles using electric current.

According to the invention the object is solved in that at least one electrode is made of a conductive synthetic material at least based on a plastic material which is doped with at least one conductive substance. To avoid the release of metal ions a conductive synthetic material being made of doped plastic is used. Thus, toxic effects, for instance on living cells, such as during the release of $Al^{3+}$ ions can be avoided. Medical compatibility of the generating products can also be enhanced this way so that, for example, the possible use of transfected primary cells for ex vivo gene therapy is supported. As a result of doping the plastics with conductive substances, a current flow between both electrodes could be achieved during discharge, which is equal to the current flow using commonly used cuvettes having metal electrodes. Surprisingly, it has been determined that using the used doped plastic material with electroporation better results in respect of the transfection efficiencies can be achieved if compared to the use of, for instance, cuvettes having electrodes made of aluminium. By avoiding the toxic effects caused by the release of metal ions the ratio of transfection efficiency to cell mortality is significantly increased. It is a further advantage of the container according to the invention that no precipitate is created in the solution during electric discharge, which could adhere to the cells and impair further analysis and use of transfected cells, respectively. Obviously, it is yet a further advantage of the container according to the invention that the buffer solution has less effect on the doped plastic electrodes used. It was actually determined that in the cause of discharge very high resistance is generated at the surface of the electrode, which, at a given start current, causes a drastical decrease of current flow, if buffers containing phosphate but no chloride are used with cuvettes made of aluminium. Surprisingly, this can be avoided by using the container and electrodes according to the invention, respectively. The containers according to the invention are thus merely affected by the conductivity of the solution but not negatively affected by the buffers used. The containers according to the invention can be injection-moulded in one mould using two-component injection moulding because doped synthetic material, in contrast to intrinsically conductive plastic, is injection-mouldable. Thus, the container according to the invention can be produced in an easy and cost effective manner. The doped plastic material may have a density, for example, between 1.3 and 1.5 $g/cm^3$, preferably a density of 1.37 or 1.54 $g/cm^3$, and a melting temperature of 230 to 310° C. Preferably, the doped plastic material has a specific forward resistance of 2 Ohm×cm or less, and a specific input resistance of $10^4$ Ohm or less.

In respect of the conductivity of the synthetic material it turned out to be particularly advantageous if the dope consists of carbon fibers, graphite, soot, carbon nanotubes and/or an intrinsically conductive synthetic material. The overall concentration of the dope in the plastic material should be in the range between 10 and 80% w/w. The conductivity of the synthetic material is not sufficient below a percentage of 10%, while the possibility to injection-mould the synthetic material is extremely reduced above a percentage of 80%. Using the container according to the invention with electroporation or electrofusion of cells, derivatives of cells, subcellular particles and/or vesicles it has been shown that it is particularly advantageous in respect of conductivity that the overall concentration of the dope is 20-60% w/w, more preferred 40-60% w/w, particularly preferred 50-60% w/w, in particular 55-60% w/w.

Several applications, in particular transfection of DNA into the nucleus of primary cells, need particularly high electric currents and field strengths, respectively, in the solution to achieve sufficiently high efficiencies. In these cases it is advantageous if the overall concentration of the dope in the plastic material is between 40 and 80% w/w. This ensures a high conductivity of the electrodes so that flow of sufficiently high currents through the solution and the inner space of the container, respectively, is possible. In an advantageous embodiment of the invention the concentration of the dope may be in the range of 50-80% w/w, preferably 60-80% w/w, more preferred 70-80% w/w, in particular 74-76% w/w, depending on the application and the type of the cells to be treated. A sufficient injection-mouldability of the material is ensured in this respect even if the dope has high concentrations up to 80% w/w. In this respect, the use of particular mixtures of dopes, e.g. carbon fibers and graphite, may have a positive influence on mouldability.

In respect of the injection-mouldability of the synthetic material it turned out to be particularly advantageous if the plastic material is polycarbonate, polyetheretherketone, polypropylene, polyamide, polyphenylensulfide or a mixture of these polymers, or at least based on one or several of these polymers, and/or wherein said plastic material is an intrinsically conductive synthetic material. In this respect, the use of polyamide 66 or polyamide 6 is particularly advantageous.

If the synthetic material itself is doped with an intrinsically conductive synthetic material, an advantageous embodiment of the invention is provided, wherein the intrinsically conductive synthetic material is polyaniline, polyacetylene, poly-para-phenylene, poly-para-phenylensulfide, polypyrroles, polythiophene, polypropylene or the like, or at least based on one or several of these polymers.

In another advantageous embodiment of the invention it is provided that the outer limit is made of synthetic material, preferably transparent plastic material, because it is thus possible to produce the entire container using injection moulding methods. It may be advantageous in this respect if the outer limit is made of the same plastic material as the plastic material on which the at least one electrode is based. In this embodiment there may be benefits with the processing of the synthetic material using two-component injection moulding. Thereby, on the one hand the production is simplified and on the other hand the production costs are reduced. However, for special applications, the outer limit may consist of other material as well.

In a particularly advantageous embodiment of the invention it is provided that the at least one electrode is integrated into said outer limit so that the container can be injection-moulded in one mould.

In a preferred embodiment of the invention it is provided that the container comprises at least two electrodes being made of the same material. Most applications use containers and cuvettes, respectively, which have two oppositely arranged, parallel electrodes consisting of the same material. These two electrodes are contacted in a suitable manner and thereby connected to a voltage source adapted to the respective requirements. However, in special cases it may also be beneficial if at least two electrodes are made of different materials. In these cases, the anode or the kathode may consist of the doped synthetic material while the respective counter electrode may consist of another material, e.g. stainless steel or an intrinsically conductive synthetic material.

The containers comprising electrodes made of a conductive synthetic material according to any one of the claims 12 to 18 proved to be particularly advantageous for transfection of living cells. These containers have a high conductivity combined with electrode material which is easily processable.

In an alternative embodiment of the invention it is provided that the outer limit comprises at least one opening for supplying the solution and at least one opening for draining off the solution. The container according to the invention can thereby also be used as flow-through container with which the solution flows through the inner chamber continuously or discontinuously.

The containers according to the invention are advantageously suitable in the form of container arrangements comprising at least two, preferably 6, 12, 24, 48, 96 or more, containers being joined to build one unit, i.e. so-called "multiwells".

It is a particular advantage of the invention that the containers or container arrangements according to the invention can be produced using a method, wherein the container or the container arrangement is produced by two-component injection moulding, wherein at first the outer limit is injection-moulded leaving one recessed window and the conductive synthetic material being made of doped plastic is subsequently injection-moulded into this at least one window, or wherein at first the at least one electrode is injection-moulded of the doped plastic material and the outer limit is subsequently injection-moulded around the at least one electrode. Contrary to the production of containers or cuvettes with electrodes consisting of metal, with which the electrodes have to be manually or automatically placed into the moulded frame or mould before or after moulding of the container, the invention provides a very easy and cost-effective method of production. The containers or container arrangements according to the invention can be injection-moulded in one mould in a two-step method so that the costs of their production are significantly lower as the usual costs for the production of electroporation or elektrofusion cuvettes.

Advantageously, the containers or container arrangements according to the invention are particularly suitable for use in methods for treatment of cells, derivatives of cells, subcellular particles and/or vesicles by means of electric current, in particular for electroporation or electrofusion, wherein the cells, derivatives of cells, subcellular particles and/or vesicles are transferred into an inner chamber of at least one container or at least one container of a container arrangement, wherein said container comprises at least one electrode being made of a doped synthetic material, and at least one further electrode, and wherein a voltage is then applied to said electrodes and a current flow is generated in the inner chamber of said container. In this method, the electric current may reach a current density up to 120 A/cm$^2$, preferably 80 A/cm$^2$, and the cells, derivatives of cells, subcellular particles and/or vesicles may be provided in suspension, or adhered or in otherwise immobilized condition.

Accordingly, beside other possible applications, the containers or container arrangements according to the invention are suitable, for instance, for electroporation, i.e. methods for introducing biologically active molecules into living cells using electric current, wherein biologically active molecules, in particular nucleic acids, are solved in said solution, and transfer of said biologically active molecules into living cells is achieved by means of a voltage pulse having a field strength of 2 to 10 kV*cm$^{-1}$ and a duration of 10 to 200 μs. Subsequently, a current flow following said voltage pulse without interruption, having a current density of 2 to 14 A*cm$^{-2}$, preferably 5 A*cm$^{-2}$, and a duration of 1 to 100 ms, preferably 50 ms, can be provided. In this method, the cells can be used, for example, in suspension or as an adhering cell layer.

The containers or container arrangements according to the invention are also suitable, for instance, for electrofusion, e.g. methods for fusion of cells, derivatives of cells, subcellular particles and/or vesicles using electric current, wherein the cells, derivatives of cells, subcellular particles and/or vesicles, for example, are suspended at a suitable density in an aqueous solution, said suspension is subsequently transferred into a container or container arrangement according to the invention, and finally an electric voltage is applied to the electrodes generating a current flow through the solution. Alternatively, for example, also adhering cells, derivatives of cells, subcellular particles and/or vesicles can be fused as well as, for example, adhering cells with suspended cells, derivatives of cells, subcellular particles or vesicles.

BRIEF DESCRIPTION OF THE DRAWINGS

The invention is described below in detail with reference to the drawings.

In the figures

DESCRIPTION OF VARIOUS AND PREFERRED EMBODIMENTS OF THE INVENTION

Figure 1:
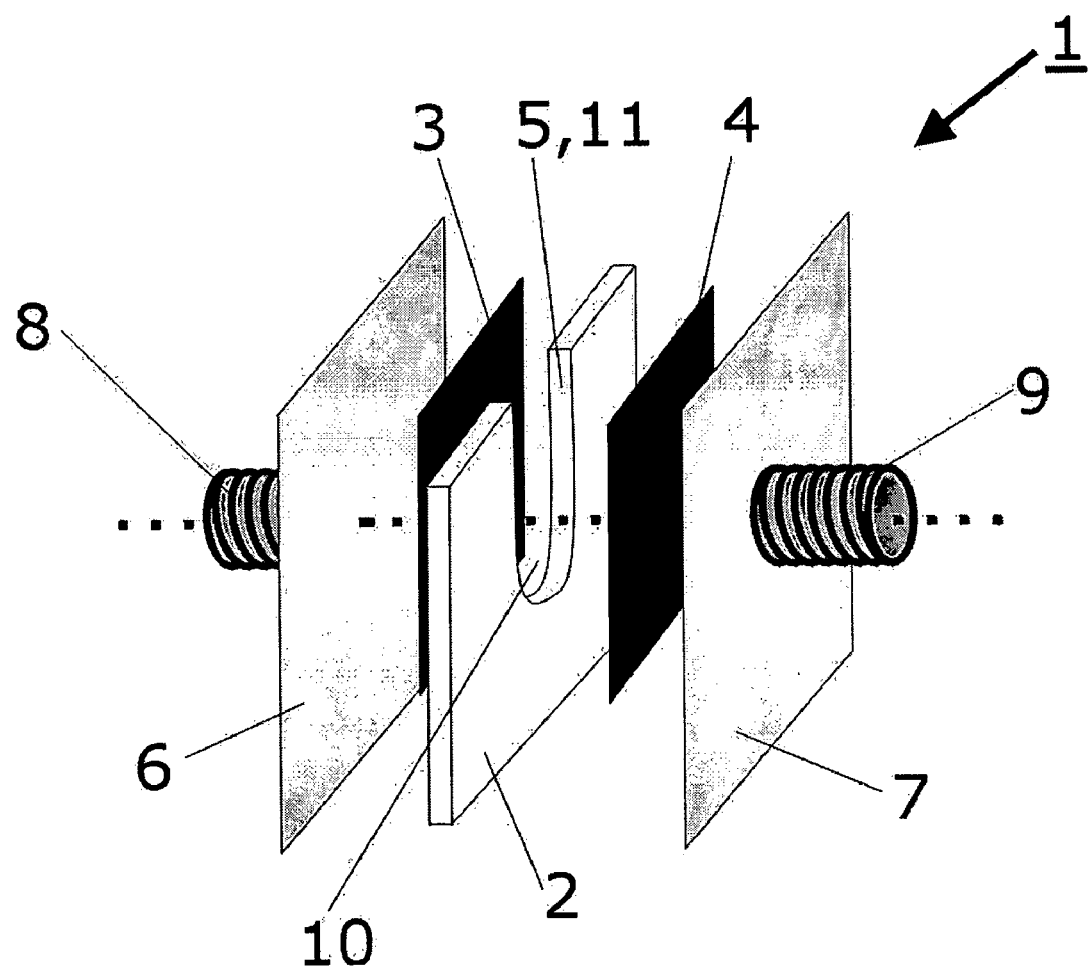
FIG. 1 is a perspective representation of an experimental assembly for demonstration of the present invention.

FIG. 1 shows a perspective representation of an experimental assembly 1 for demonstration of the present invention and for testing of the containers according to the invention, respectively. The experimental assembly 1 is equivalent to the construction of the containers according to the invention and comprises a spacer plate 2 and two electrodes 3, 4 being pressed against both sides of the spacer plate 2. The spacer plate 2 is a plate made of Teflon having a thickness of 2 mm, which has an U-like formed recess 5. The electrodes 3, 4 consist of a synthetic material which is doped with at least one conductive substance. The synthetic material may be, for example, polycarbonate, polyetheretherketone, polypropylene, polyamide, polyphenylensulfide or a mixture of these polymers and/or an intrinsically conductive synthetic material. The three layers which include the spacer plate 2 and both electrodes 3, 4 are pressed together at both sides like a sandwich by the copper plates 6, 7. For this purpose, the copper plates 6, 7 are moved towards the other by the threaded parts 8, 9 of a vise-like device (not shown). When the above-named layers are pressed together an inner space 10 is then formed in the range of the recess 5, which has the capacity to receive the solution and cells, respectively. In the depicted model the inner space 10 can receive a volume of 100 ml. The inner space 10 is further formed at the bottom and at both sides by the inner edges 11 of the spacer plate 2, and at the two remaining sides by the electrodes 3, 5. The copper plates 6, 7 are electrically contacted via two wires to spring contacts of a customary electroporation device, i.e. a voltage source. The electrodes 3, 4 themselves are in direct contact to the copper plates via their entire outer surface so that the best electric contact is ensured. Thus, using the experimental assembly 1 as shown, a current flows between the electrodes 3, 4 through the inner space 10 filled with the solution and the cell suspension, respectively, if a voltage pulse is applied to the copper plates 6, 7.

Figure 2:
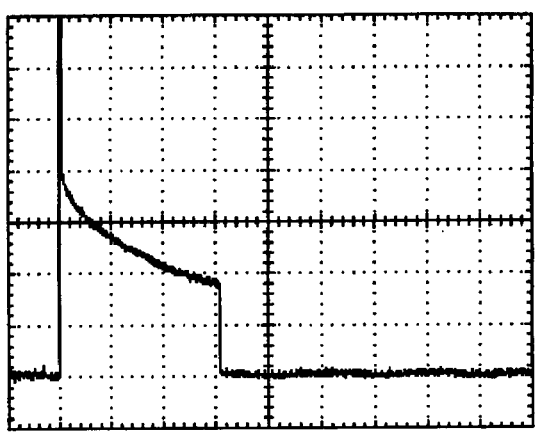
FIG. 2 shows the current flow of electric discharges using electrodes according to the invention, which are made of polycarbonate including 20% carbon fibers and 15% graphite (PC+CF+Gr having an electrode thickness of 1.65 mm), compared to the usage of electrodes made of aluminium, respectively with two different buffer solutions (Solution A: 100 mM sodiumphosphate, pH 7.1, and 25 mM potassiumchloride; Solution B: 140 mM sodiumphosphate, pH 7.1; Ordinate: current, 1 A per square; Abscissa: time, 10 ms per square)
Figure 2:
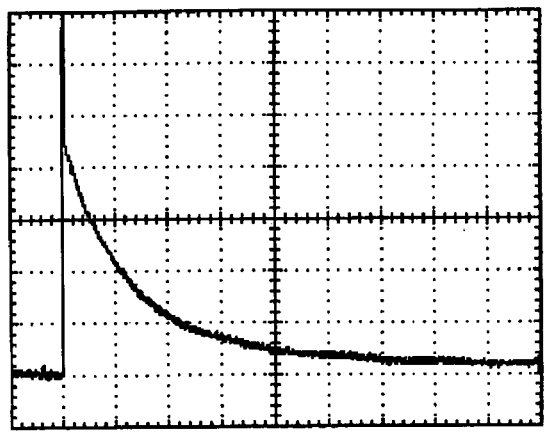
Figure 2:
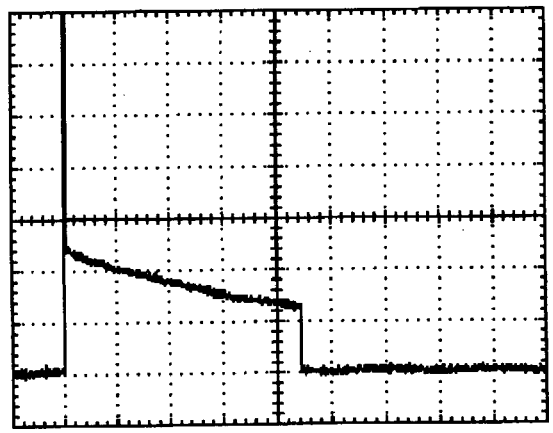
Figure 2:
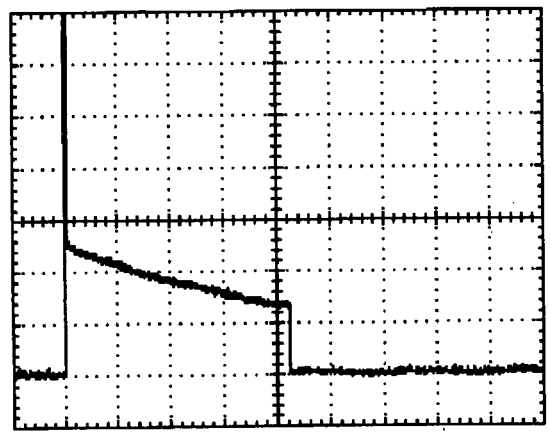

FIG. 2 shows the current flow of electric discharges using electrodes according to the invention, which are made of polycarbonate with 20% carbon fibers and 15% graphite (PC+CF+Gr), compared to the use of electrodes made of aluminium. In this approach, the current flow through two different buffer solutions was measured (Solution A: 100 mM sodiumphosphate, pH 7.1 and 25 mM potassiumchloride; solution B: 140 mM sodiumphosphate, pH 7.1). A first voltage pulse of 1000 V and 40 µs duration was always applied followed without interruption by a second pulse having a start voltage ($U_{start}$) of 90 V and a charge of 75 mC. The respective current flow of the second pulse is shown in this representation. Surprisingly, it turned out that, if the electrodes made of synthetic material according to the invention are used, a similar current flow of that scale can be achieved under the same conditions as can be achieved with the customary electrodes made of aluminium (comparisons a and c). The doped synthetic material is thus particularly suitable for conducting high current densities in a short period of time. Using a phosphate buffer without chloride (Solution B) in contrast to the use of a phosphate buffer containing chloride (Solution A) it turned out that in the course of discharge a very high resistance is increasingly generated at the surface of electrodes made of aluminium, which causes a drastic decrease of current flow at the same start current (b). This negative effect does not occur when doped synthetic material is used (d) so that, contrary to usually used cuvettes, the containers or electrodes according to the invention are also suitable for the use of phosphate buffers without chloride. Thus, using the containers according to the invention the selection of the buffer solution is not as limited as with the use of conventional containers.

Figure 3:
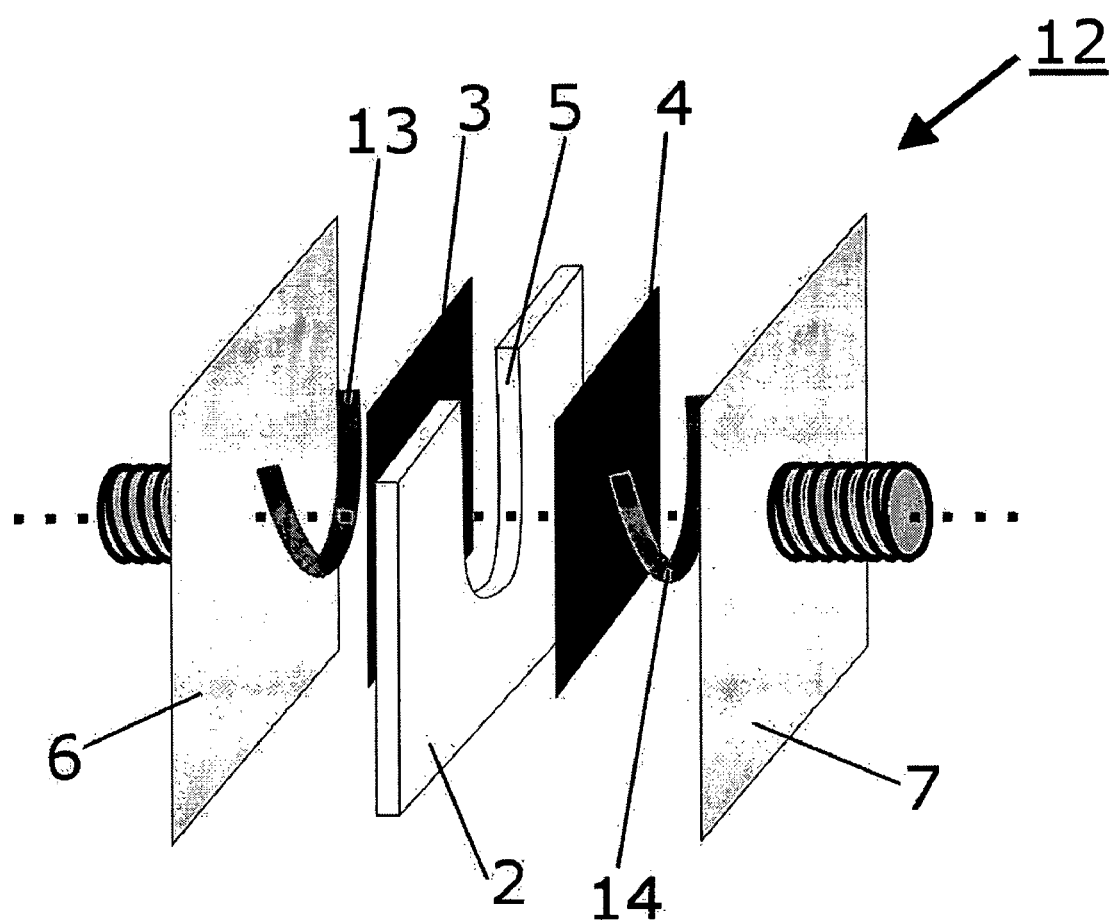
FIG. 3 is a perspective representation of an experimental assembly according to FIG. 1 modified by insertion of copper wires.

FIG. 3 shows a perspective representation of an experimental assembly 12 which is modified in comparison to the experimental assembly 1 according to FIG. 1. The experimental assembly 1 according to FIG. 1 shows an arrangement where the electrodes 3, 4 are contacted by the copper plates 6, 7 using relatively high pressure on a large surface. Since contacting of the outside of electrodes, for example with a conventional electroporation apparatus, is usually not carried out with such a high pressure on such a large surface, in this experimental assembly 12 the surfaces contacting the electrodes are designed smaller. Thus, this assembly is more equivalent to a contacting by spring contacts and hence to the actual conditions in reality. For this purpose, round and v-like bended copper wires 13, 14 having a diameter of about 1.5 mm were placed between the electrodes 3, 4 and the respective adjacently arranged copper plates 6, 7. In the following, FIG. 4 shows a comparison of the current flows if the experimental assemblies according to FIGS. 1 and 3 are used.

Figure 4:
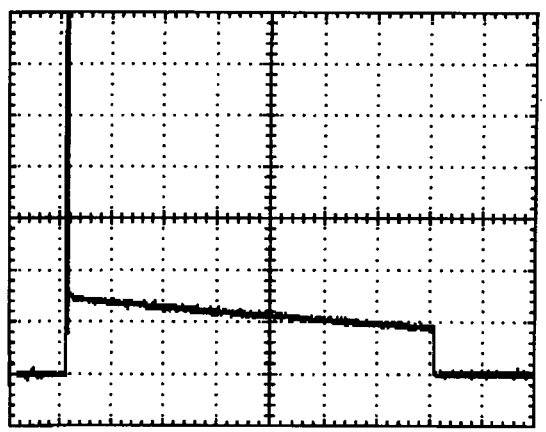
FIG. 4 shows the current flow of electric discharges using electrodes made of polycarbonate including 20% carbon fibers (Electrode thickness 2 mm), and using an experimental assembly according to FIG. 1 (a) and FIG. 3 (b), ordinate: current, 1 A per square and abscissa: time, 10 ms per square.
Figure 4:
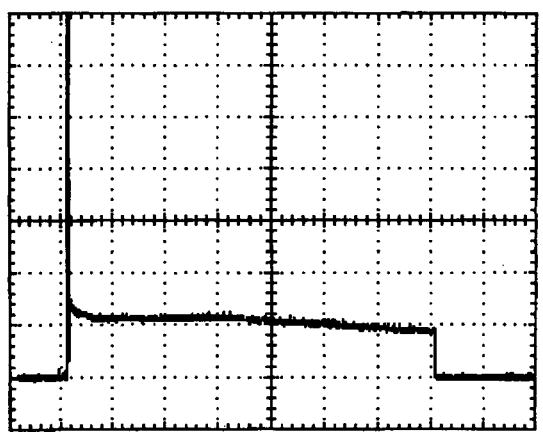

FIG. 4 shows the current flow of electric discharges using electrodes made of polycarbonate including 20% carbon fibers for the experimental assembly 1 according to FIG. 1 (a) as well as for the experimental assembly 12 according to FIG. 3 (b). The current flows of the second pulse are always shown (1. Pulse: 100 V, 40 µs; 2. Pulse: $U_{start}$=90 V, 75 mC). The constant result shows that obviously the electric potential is steadily distributed on the inside of the electrodes and the contacting surface is thus not the limiting factor in respect of conductivity.

Figure 5:
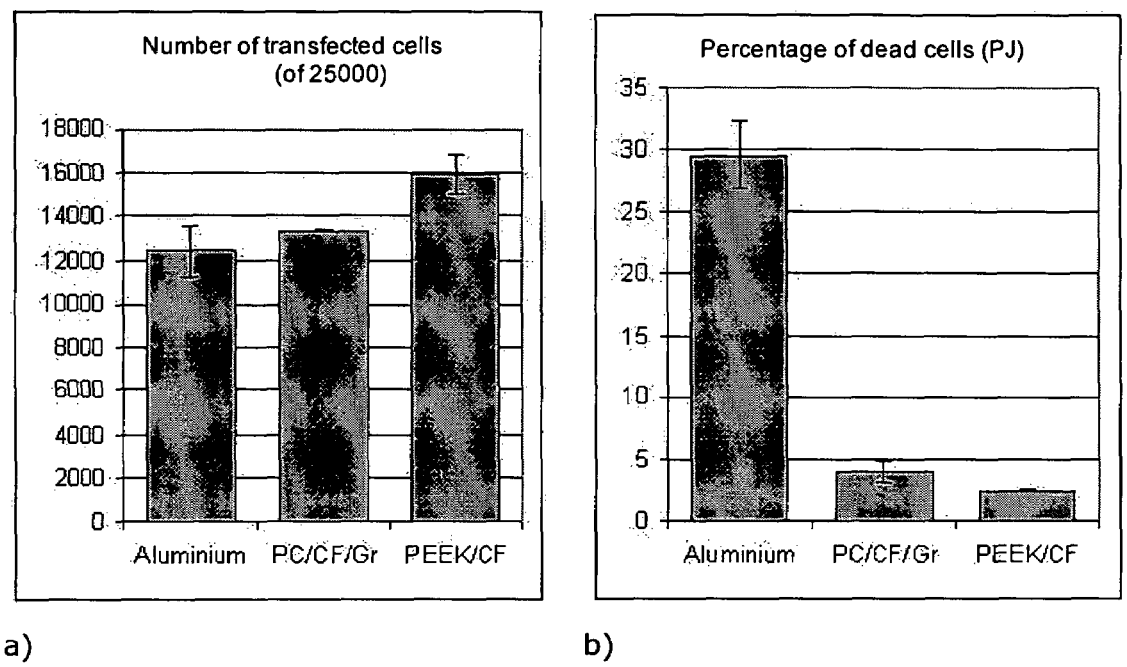
FIG. 5 shows diagrams of a flow-cytometric analysis of transfected CHO cells (Chinese hamster ovary cells) using different electrodes made of synthetic material according to the invention compared to electrodes made of aluminium, a) number of transfected cells per 25,000 cells, b) percentage of dead cells stained with propidiumjodide, PC/CF/Gr=polycarbonate+20% carbon fibers+15% graphite with an electrode thickness of 1.65 mm, PEEKIDF=polyetheretherketone+40% carbon fibers with an electrode thickness of 1 mm.

FIG. 5 shows diagrams of a flow-cytometric analysis of transfected CHO cells. Transfection experiments are conducted using the experimental arrangement described in FIG. 1 in order to biologically determine the functionality of the containers according to the invention. For this purpose, CHO cells were suspended in 100 µl of an appropriate buffer solution, for example PBS (phosphate-buffered saline), adding 5 µg of the expression plasmid pH-2K$^k$ (DNA vector which codes for the heavy chain of a mouse MHC class I protein), and then transferred into the inner space of the experimental assembly. Electroporation of the cells is then carried out by application of two pulses (1. Pulse: 1000 V, 100 µs; 2. Pulse $U_{start}$=108 V, 100 mC). The cell suspension was subsequently removed, transferred into an appropriate medium, for example RPMI medium, and harvested after 20 hours incubation at 37° C. and 5% $CO_2$. Adhering CHO cells were washed with PBS and detached using 0.1% trypsine+2 mM ethylendiamintetraacetate in PBS. The expression of H-2K$^k$ was revealed using antibody staining (1:100 anti-H-2K$^k$ (Becton Dickinson)+1:50 beriglobine (Aventis Behring) in PBS, 10 minutes at room temperature). The dead cells were stained with 0.25 µg/ml propidiumjodide. The analysis was carried out in a flow-cytometer (FACScalibur, Becton Dickinson). Diagrams a) and b) show that using electrodes with doped synthetic material (PC/CF/Gr=polycarbonate+20% carbon fibers+15% graphite and PEEK-CF=polyetheretherketone+40% carbon fibers) at least similar results can be achieved in respect of transfection efficiency compared to the use of electrodes made of aluminium. Due to the significantly lower mortality rates if electrodes according to the invention are used, a significant advantage in comparison to the use of conventional electrodes is achieved because of the better ratio of transfection efficiency to mortality.

Figure 6:
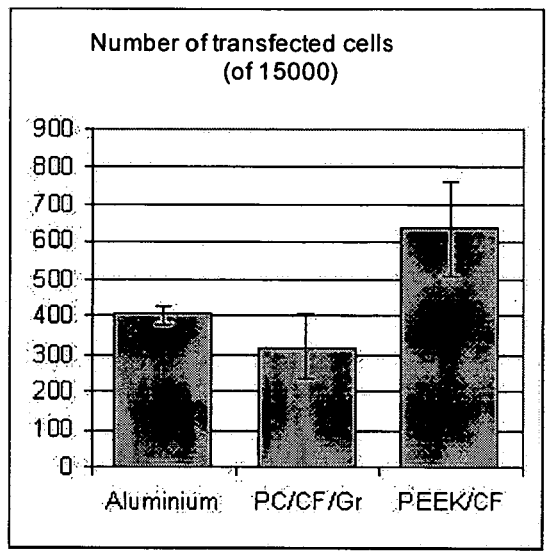
FIG. 6 shows diagrams of a flow-cytometric analysis of transfected HL-60 cells (human lymphoma cells) using different electrodes made of synthetic material according to the invention compared to electrodes made of aluminium, a) number of transfected cells per 15,000 cells, b) percentage of dead cells stained with propidiumjodide, PC/CF/Gr=polycarbonate+20% carbon fibers+15% graphite with an electrode thickness of 1.65 mm, PEEK/DF=polyetheretherketone+40% carbon fibers with an electrode thickness of 1 mm.
Figure 6:
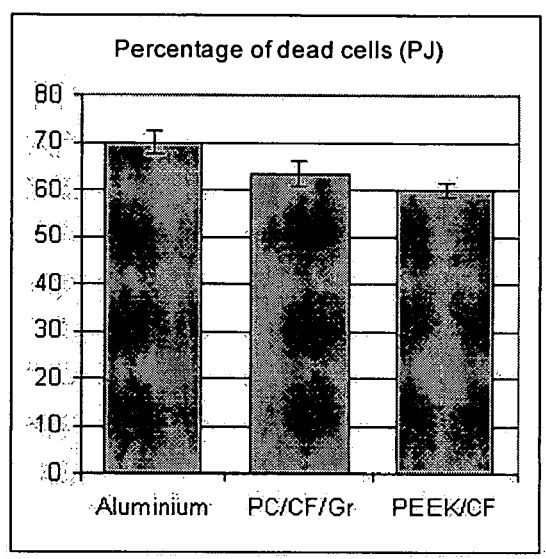

FIG. 6 shows diagrams of a flow-cytrometric analysis of transfected HL60 cells (human lymphoma cells). Realisation and conditions of this approach correspond to that described in FIG. 5 with the exception that during electroporation the voltage pulses were modified (here: 1. Pulse: 1000 V, 70 µs; 2. Pulse: $U_{start}$=81 V, 22 mC). In this approach, results could be achieved using electrodes made of doped synthetic material, which are at least similar to those if electrodes made of aluminium are used.

Figure 7:
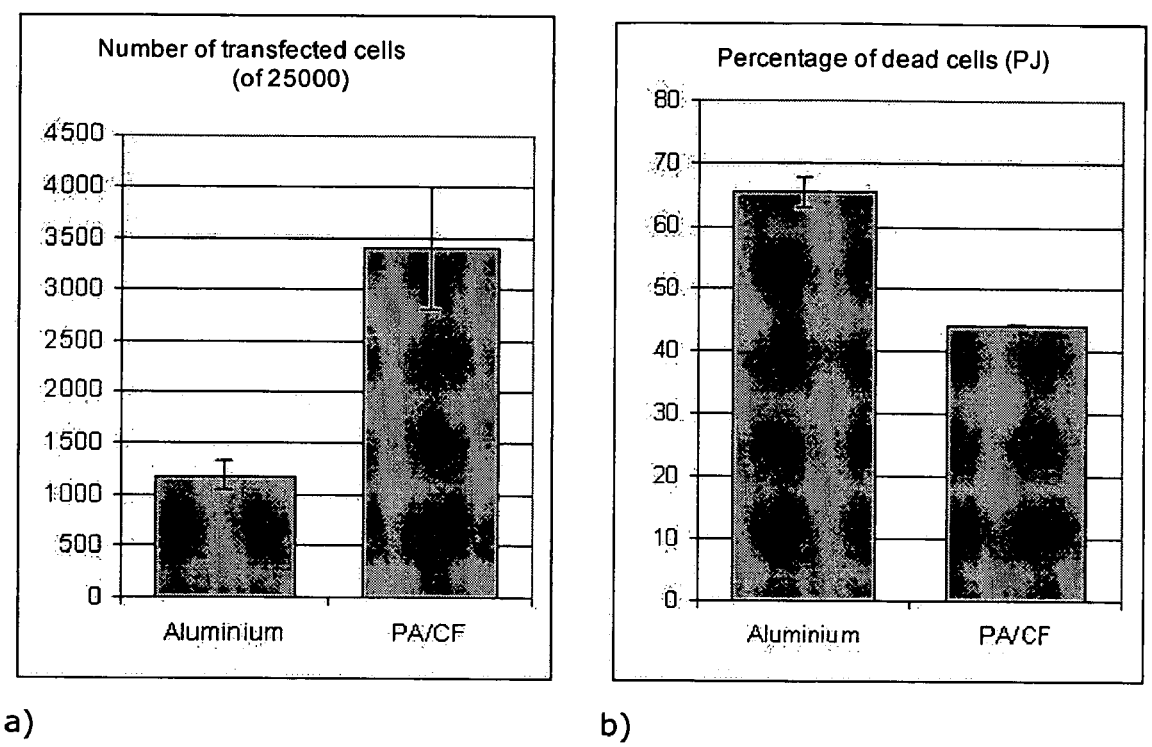
FIG. 7 shows diagrams of a flow-cytometric analysis of transfected Jurkat cells (human T-cell line) using electrodes made of synthetic material according to the invention compared to electrodes made of aluminium, a) number of transfected cells per 25,000 cells, b) percentage of dead cells stained with propidiumjodide, PA/CF=polyamide 66+30% carbon fibers with an electrode thickness of 1 mm.

FIG. 7 shows diagrams of a flow-cytometric analysis of transfected Jurkat cells (human T-cell line) using electrodes according to the invention made of polyamide 66 which was doped with 30% carbon fibers. Electroporation was carried out in 100 µl RPMI medium without phenolred with 5 µg of the plasmid pEGFP-C1 by a pulse of 150 V and 5 µs followed by a pulse having a start voltage of 108 V and a charge of 80 mC. The analysis was carried out after 4 hours. Also in this example, transfection efficiency as well as survival rate could be significantly increased by the use of containers or electrodes made of doped synthetic material according to the invention in comparison to conventional electrodes made of aluminium. Thus, the results depicted in FIGS. 5-7 clearly prove that, compared to conventional cuvettes, in electroporation the transfection efficiencies can be significantly increased and the mortality rate can be significantly decreased if the containers according to the invention are used. This can be primarily explained by the fact that, surprisingly, similar current flows can be ensured using electrodes according to the invention while the known drawbacks due to the release of metal ions from the electrodes and hence toxic effects on the cells can be avoided.

Figure 8:
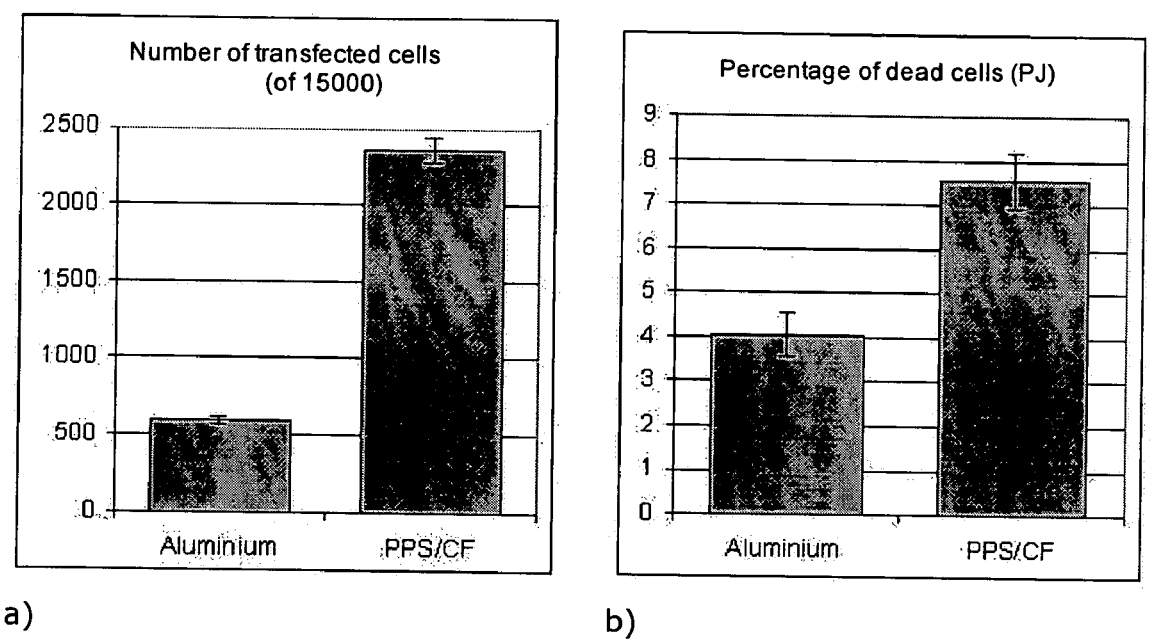
FIG. 8 shows diagrams of a flow-cytometric analysis of transfected HUVEC cells (human umbilical cord vein endothelial cells) using electrodes made of synthetic material according to the invention compared to electrodes made of aluminium, a) number of transfected cells per 15,000 cells, b) percentage of dead cells stained with propidiumjodide, PPS/CF=polyphenylensulfide+40% carbon fibers.

FIG. 8 shows diagrams of a flow-cytometric analysis of transfected HUVEC cells (human umbilical cord vein endothelial cells) using electrodes made of polyphenylensulfide with 40% carbon fibers according to the invention compared to conventional electrodes made of aluminium. Transfection was performed in a cell specific medium including 5 µg/100 µl plasmid DNA, wherein in this approach various voltage pulses were applied for compensation of the somewhat lower conductivity of the doped synthetic material (Pulse for PPS/CF: 1000 V, 100 µs; Pulse for aluminium: 500 V, 100 µs). After 60 hours incubation the cells were flow-cytometrically tested for expression of a fluorescent protein. Dead cells were stained with 0.25 µg/ml propidiumjodide in this approach as well. The results show that the containers according to the invention are generally also suitable for primary human cells. Also in this approach, the ratio of transfection efficiency to mortality rate is better than with the use of conventional electrodes made of aluminium. This effect can be further enhanced by compensation of the effectively higher resistance of the doped synthetic material by increasing the applied voltage. By this measure, the electric conditions within the cell suspension can be adapted if electrodes made of doped synthetic material are used and the transfection efficiency can be further increased.

Figure 9:
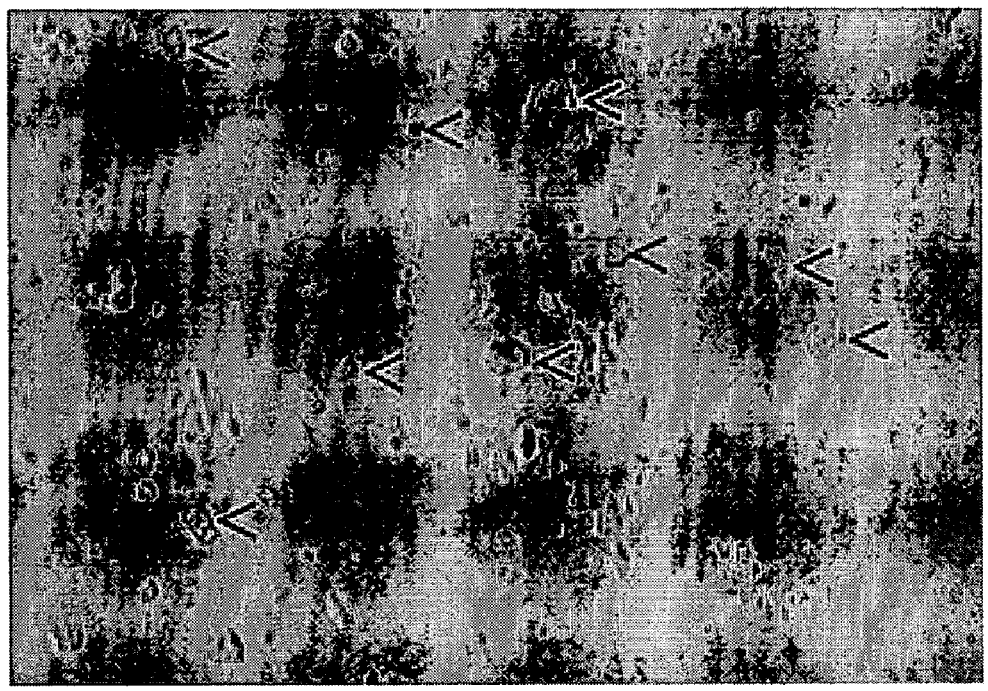
FIG. 9 is a micrograph of CHO cell cultures (CHO=Chinese hamster ovary cells) 2 days after electroporation using a) electrodes made of aluminium and b) electrodes made of polyphenylensulfide+40% carbon fibers.
Figure 9:
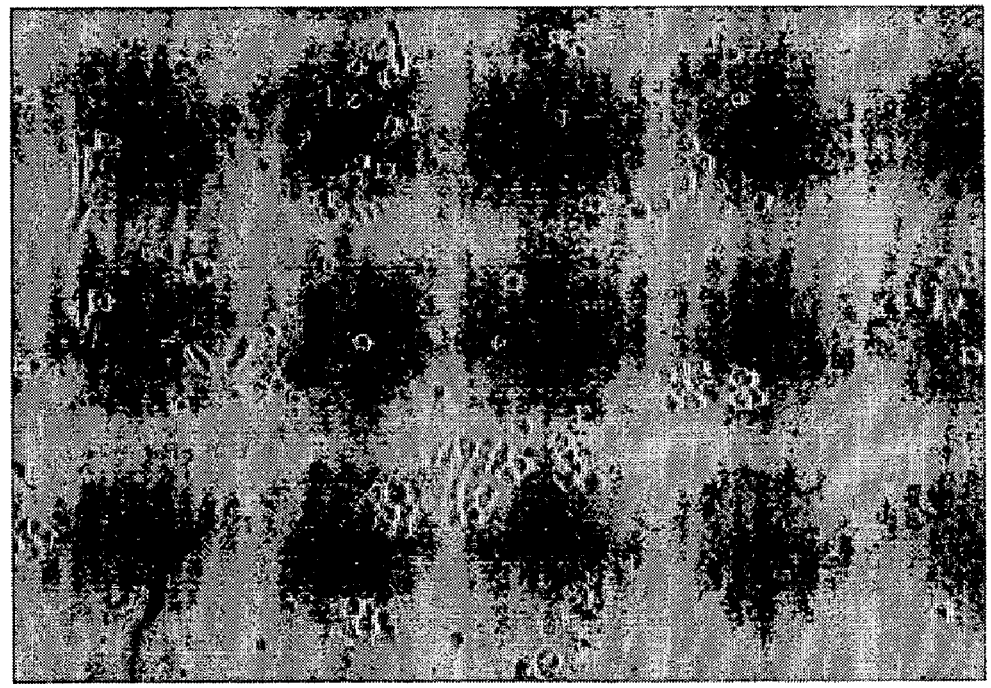

FIG. 9 shows micrographs of CHO cultures always two days after electroporation using electrodes made of aluminium (a) and electrodes made of polyphenylensulfide including 40% carbon fibers (b). Also in this approach, the somewhat lower conductivity of electrodes made of doped synthetic material was compensated by an increase of the first and second voltage pulses (PPS/CF: 1000 V, 100 µs and $U_{start}$=108 V, 100 mC; Aluminium: 500 V, 100 µs and $U_{start}$=76 V, 60 mC). Precipitates are clearly visible when electrodes made of aluminium are used, some of them being marked by inserted arrows in a). These particles precipitate onto the cells. But those particles are not visible if electrodes made of doped synthetic material are used so that precipitation of particles can be obviously avoided by the use of the container according to the invention. This fact has a positive effect on the survival rate of the cells and it is also beneficial for the further handling of the cells. Medical compatibility of the electroporation products is hereby also enhanced so that, for example, the possible use of transfected primary cells for ex vivo gene therapy is affected particularly advantageous.

Figure 10:
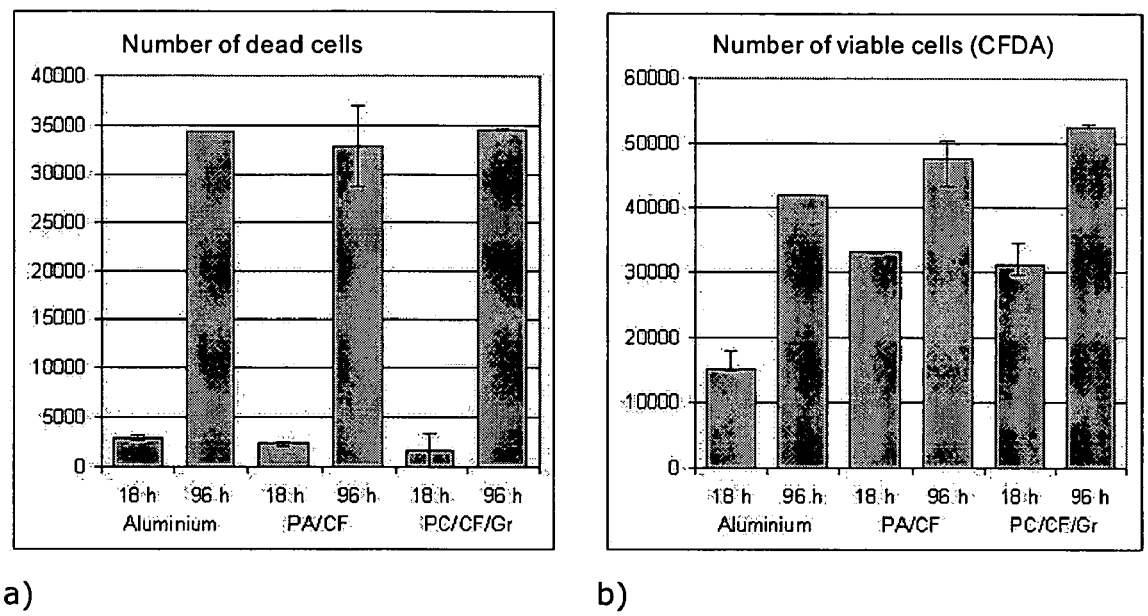
FIG. 10 shows diagrams of a flow-cytometric analysis of HUVEC cells (human umbilical cord vein endothelial cells) after incubation in differently treated solutions, a) number of dead cells stained with propidiumjodide, b) number of living cells stained with carboxyfluoresceindiacetate-succinimidylester (CFDA-SE), PA/CF=polyamide 66+30% carbon fibers with an electrode thickness of 1 mm, PC/CF/Gr=polycarbonate+20% carbon fibers+15% graphite with an electrode thickness of 1.65 mm.
Figure 11:
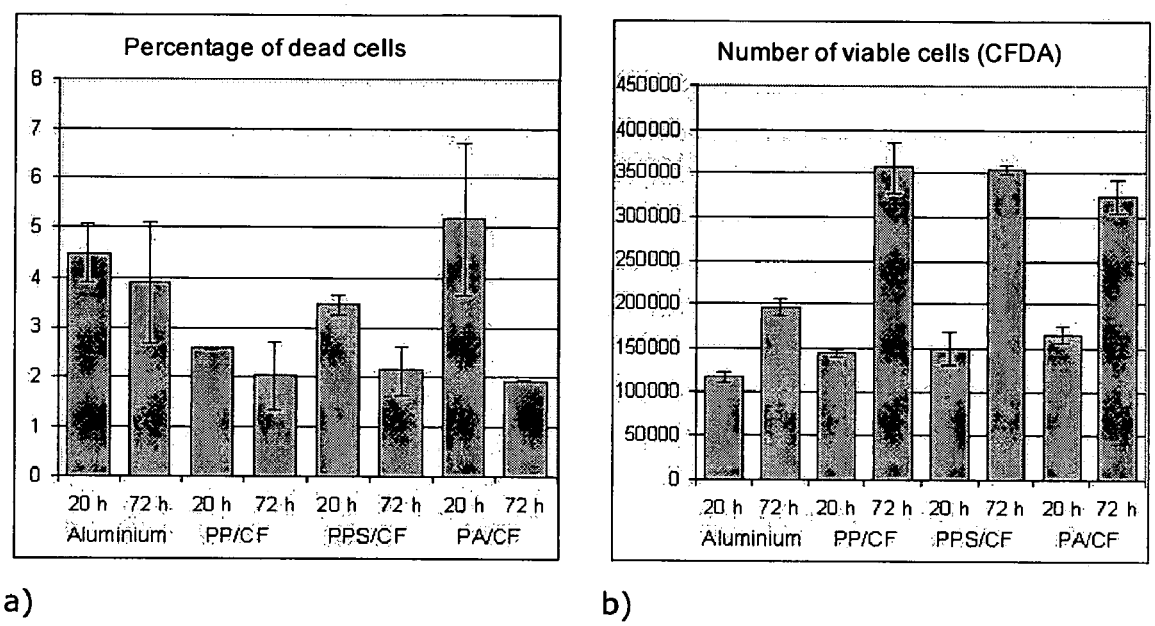
FIG. 11 shows diagrams of a flow-cytometric analysis of CHO cells (Chinese hamster ovary cells) after incubation of differently treated solutions, a) number of dead cells stained with propidiumjodide, b) number of living cells stained with carboxyfluoresceindiacetate-succinimidylester (CFDA-SE), PP/CF=polypropylene+20% carbon fibers with an electrode thickness of 1 mm, PPS/CF=polyphenylensulfide+40% carbon fibers, PA/CF=polyamide 66+30% carbon fibers with an electrode thickness of 1 mm.

FIGS. 10 and 11 each show diagrams of a flow-cytometric analysis of cells (FIG. 10: HUVEC cells, FIG. 11: CHO cells) which were incubated in differently treated solutions. The containers according to the invention were filled with simple buffer solutions, such as PBS, without cells and exposed to a high voltage pulse three times in a row (Aluminium: 500 V, 100 µs and $U_{start}$=115 V, 100 mC; doped synthetic material: 1000 V, 100 µs and $U_{start}$=95 V, 112 mC) in order to analyse the effects of possible cell-damaging components which could be released during an electric discharge from various electrodes made of doped synthetic material and from electrodes made of aluminium and which in addition to their direct effects reveal further effects on the cell culture just after the pulses. Subsequently, 100 µl of the solutions pulsed by the various electrodes were added to 400 µl culture medium (EGM-2 BulletKit/Clonetics). HUVEC cells (values after 18 hours: $5 \times 10^4$ cells, values after 96 hours: $2.5 \times 10^4$ cells) and CHO cells (values after 20 hours: $10^5$ cells, values after 72 hours: $2 \times 10^4$ cells), respectively, were transferred into 24-well plates in these media. The number of dead cells and living cells, respectively, was flow-cytometrically determined after various times of incubation at 37° C. and 5% $CO_2$. After detaching the cells using 1 µg/ml trypsin in 1 mM Ethylendiaminthetraacetate in PBS and mixture of these cells with the culture supernatant, 0.25 µl/ml propidiumjodide was added for determination of dead cells. For staining of living cells, 0.2 µM carboxyfluoresceindiacetate-succinimdylester (CFDA-SE) in PBS +0.5% bovine serum albumin were added and incubated for 2 minutes at room temperature before the flow-cytometric analysis. In order to determine the total number of cells in one probe a defined number of Flow-Count Fluorosphere Beads (Beckman Coulter) was added, which can be distinguished from the cells in the FACS. The counted number of cells could be extrapolated this way to the whole volume in one well. The results represented in FIGS. 10 and 11 show that there is a slight advantage with the use of electrodes made of doped synthetic material if compared to electrodes made of aluminium. In particular, after 4 days the solutions pulsed using electrodes made of synthetic material are more beneficial in respect of survival and growth of CHO cells. With HUVEC cells a positive effect of the plastic electrodes used in comparison to conventional electrodes made of aluminium can be already observed after 24 hours. Thus, these results are an indication for a better compatibility of electrodes made of doped synthetic material in respect of the release of cell-damaging components, wherein the negative effects after the current flow have been investigated in this approach. Due to the avoidance of the release of toxic metal ions a better biological compatibility of the containers according to the invention is additionally achieved. Thus, these are primarily with respect to the further use of transfected cells, for example the use of transformed primary cells for ex vivo gene therapy, significantly more advantageous than conventional containers or cuvettes.

Figure 12:
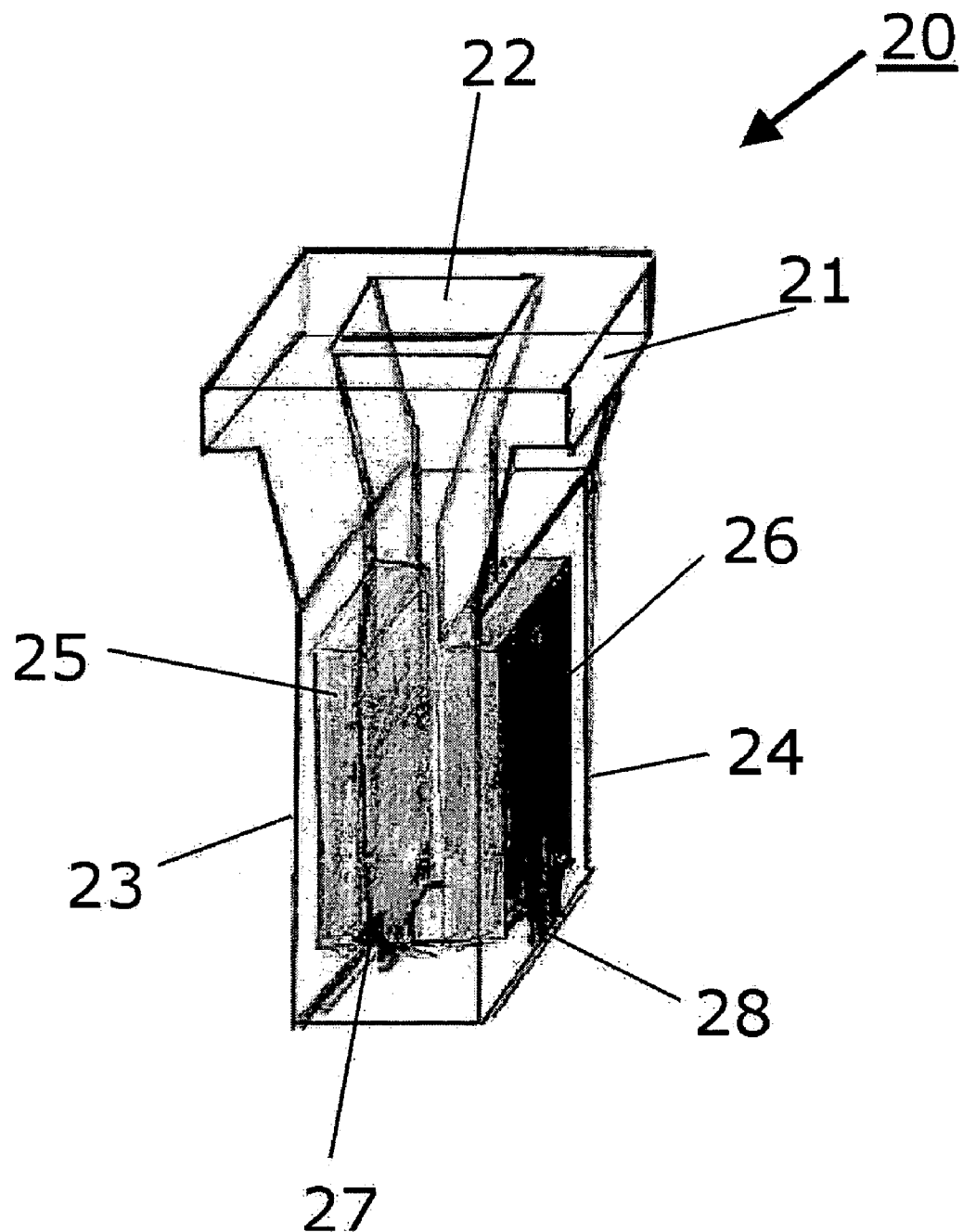
FIG. 12 is a perspective representation of one possible embodiment of the container according to the invention.

FIG. 12 shows a perspective representation of one possible embodiment of a container according to the invention. The container 20 shown is generally formed like a conventional cuvette. The container is formed by an outer limit 21 which builds an inner chamber 22 which has the capacity for receiving an aqueous solution. For example, cells, derivatives of cells, subcellular particles and/or vesicles can be suspended in this aqueous solution. In addition to the aqueous solution or suspension, the container may also contain, for instance, adhering cells, derivatives of cells, subcellular particles and/or vesicles. Two parallel electrodes 25, 26 are disposed in two parallel and oppositely arranged sidewalls 23, 24 of the outer limit 21. Both electrodes 25, 26 are made of a synthetic material which, according to the invention, is doped with at least one conductive substance. The dope may consist of, for instance, carbon fibers, graphite, soot, carbon nanotubes or an intrinsically conductive synthetic material, or a combination of one or several of these substances as well. The outer limit 21 consists of an transparent plastic material which is not electroconductive. Due to the injection-mouldability of all components the container 20 according to the invention can be produced using two-component injection moulding. In this case, at first the outer limit 21 was injection-moulded using an non-conductive plastic. The doped synthetic material being injection-mouldable as well was injection-moulded into recessed windows (which are not visible any more) through injection moulding channels 27, 28. Thus, a very simple and cost-effective production of the container 20 according to the invention is possible. Such container 20 being formed like a cuvette is primarily beneficial if it shall be used in a conventional electroporation device. However, depending on the kind of application, the container according to the invention comprises all possible embodiments that make sense anyway.

Figure 13:
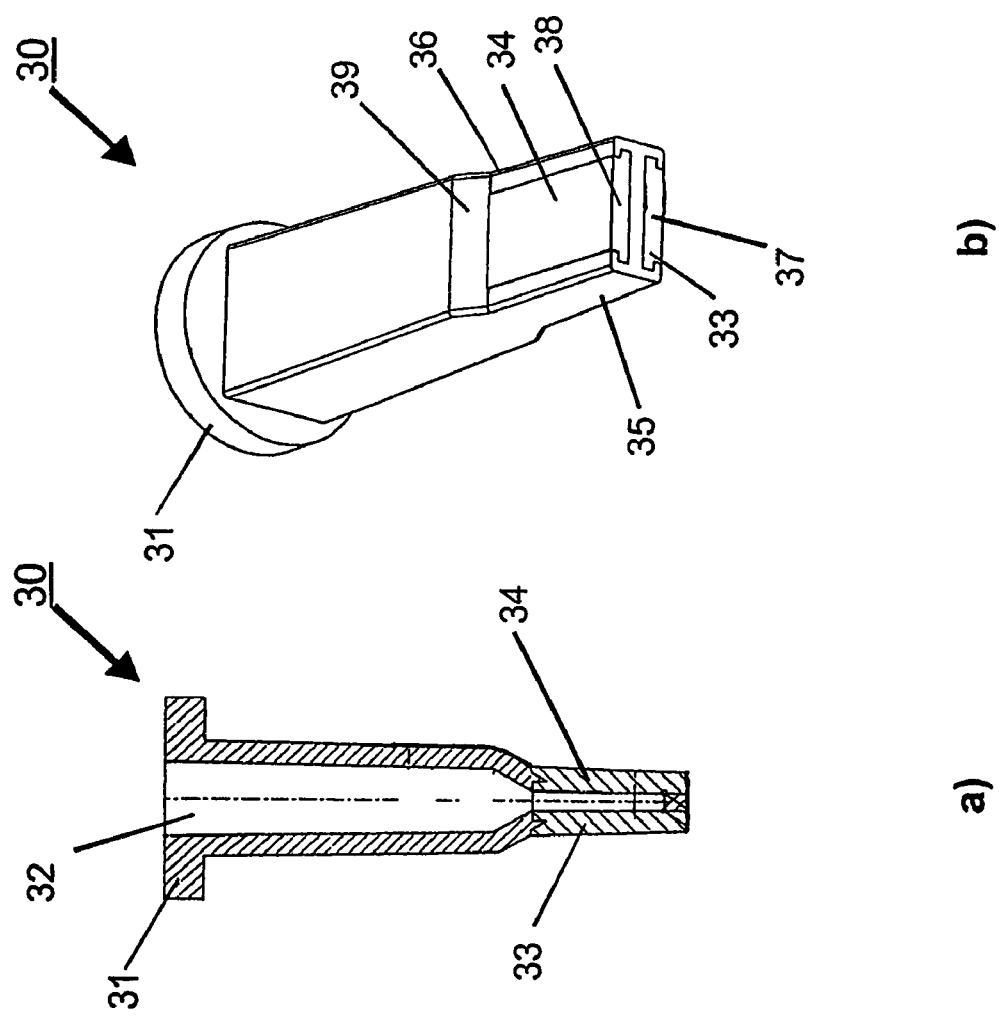
FIG. 13 is a sectional (a) and a perspective (b) representation of a further embodiment of a container according to the invention in the form of a cuvette.

FIG. 13 shows a perspective representation (b) of a possible embodiment of a container according to the invention as well as a longitudinal section (a) of the same. The container 30 shown is also formed like a cuvette. The container is formed by an outer limit 31 which builds an inner chamber 32 which acts for receiving an aqueous solution. Two parallel electrodes 33, 34 are disposed in two parallel and oppositely arranged sidewalls 35, 36 of the outer limit 31. Both electrodes 33, 34 consist of a synthetic material, for example polyamide 66 or polyamide 6, which is doped with at least one conductive substance according to the invention. In an advantageous embodiment of the invention the dope may be, for instance, a mixture of carbon fibers and graphite. The outer limit 31 consists of a transparent plastic material which is non-electroconductive. Because of the injection-mouldability of all components the container 30 according to the invention can be produced using two-component injection moulding. Hence, at first the outer limit 31 can be injection-moulded of a non-electroconductive plastic material. The doped synthetic material which is also injection-mouldable may be subsequently injection-moulded in recessed windows through injection moulding channels 37, 38. Thus, very simple and cost-effective production of the container 30 according to the invention is possible this way. An oblique part 39 is disposed in the lower half of the container 30, which enables the container 30 to be adapted to the geometry of the respective receiving element of the device used, i.e. an electroporator. Additionally, the distance between the electrodes 33, 34 may be varied by different designs of the oblique part 39 so that the forward resistance can be changed.

Figure 14:
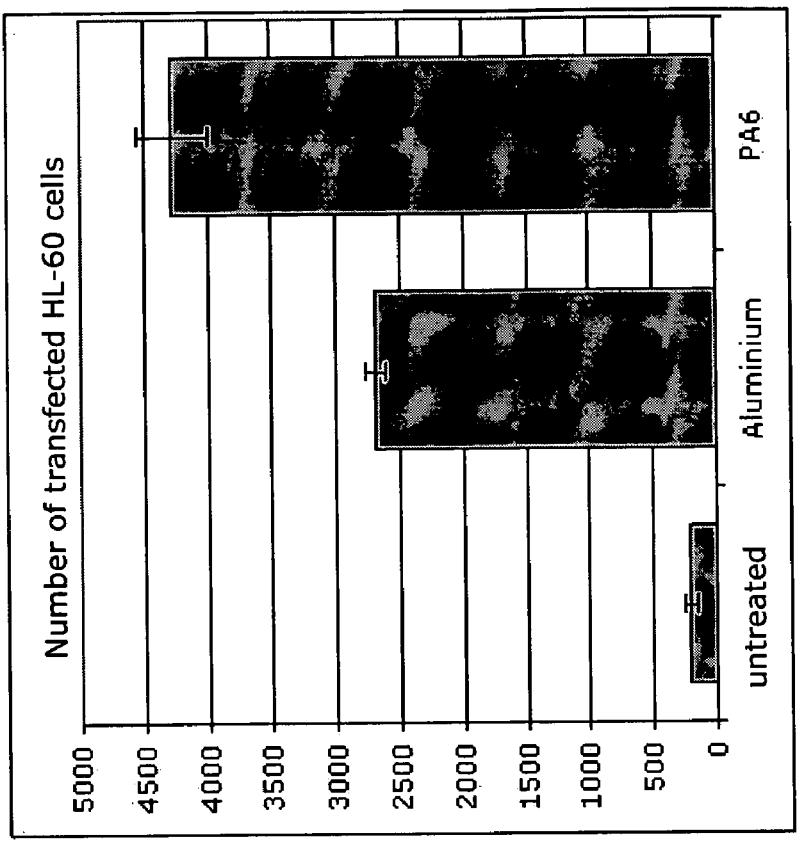
FIG. 14 shows diagrams of a flow-cytometric analysis of HL-60 cells (human lymphoma cells) after electroporation using electrodes made of synthetic material according to the invention (PA6) compared to electrodes made of aluminium, a) number of dead cells stained with propidiumjodide, b) number of transfected living cells, untreated=respectively without application of a voltage pulse.
Figure 14:
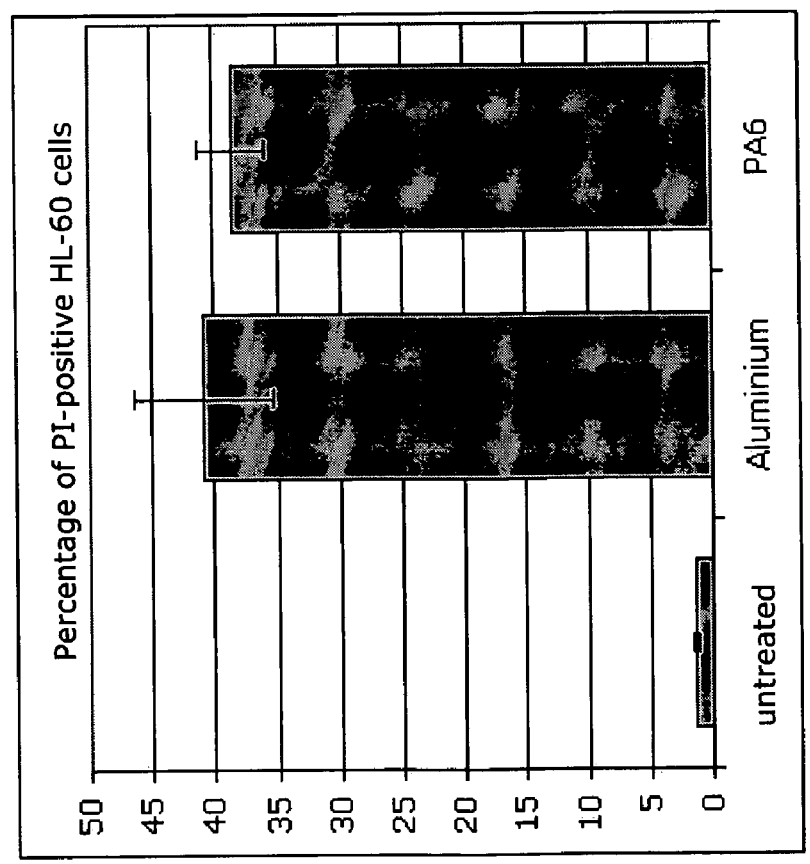
Figure 15:
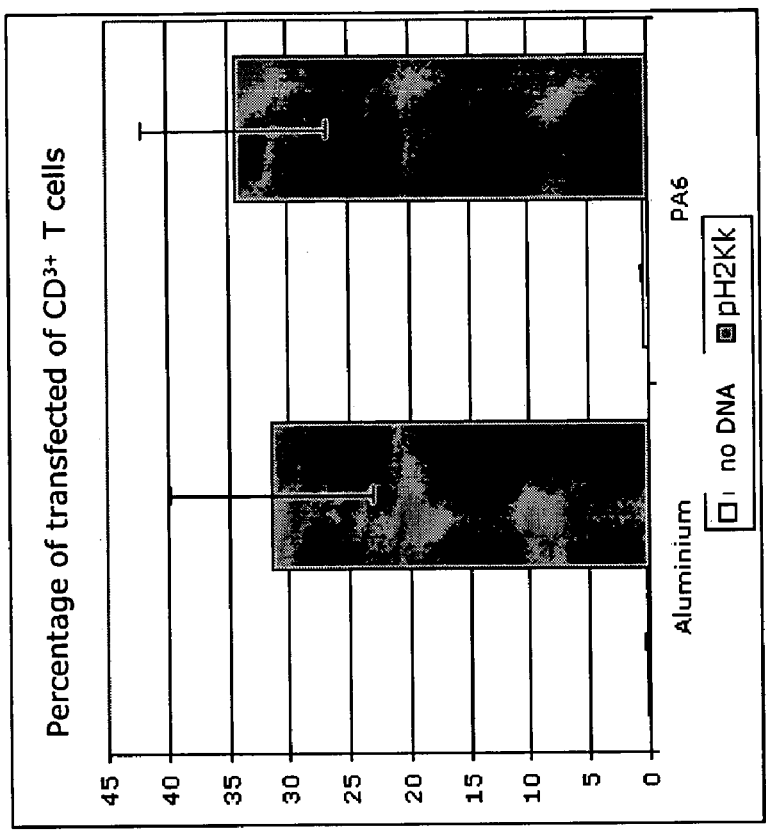
FIG. 15 shows diagrams of a flow-cytometric analysis of $CD3^+$ T-cells after electroporation using electrodes made of synthetic material according to the invention (PA6) compared to electrodes made of aluminium, a) number of dead cells stained with propidiumjodide, b) number of transfected living cells, respectively with or without vector $pH2-K^k$.
Figure 15:
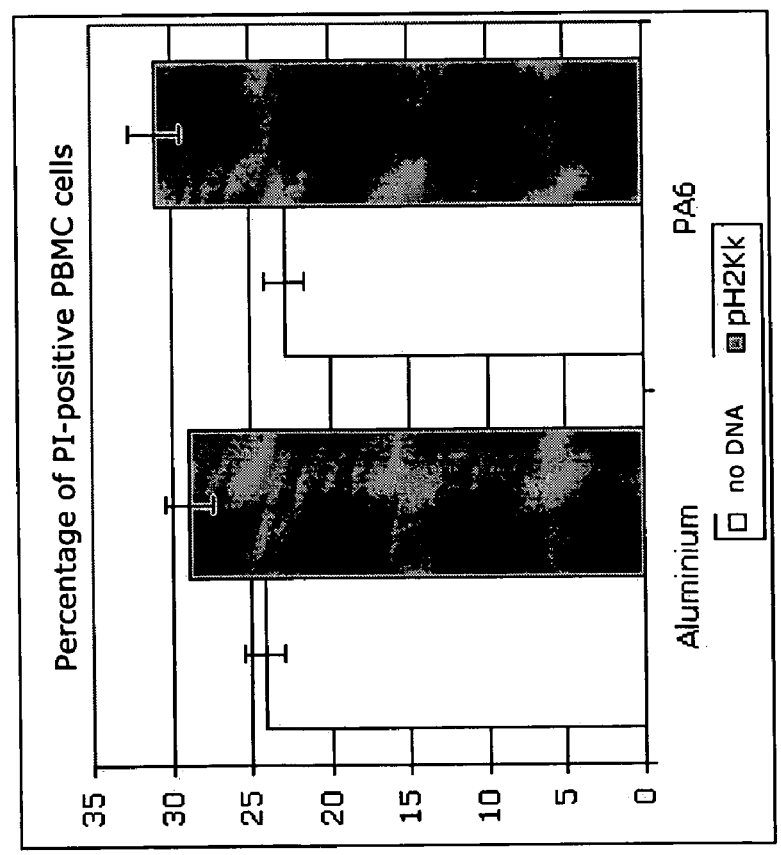
Figure 16:
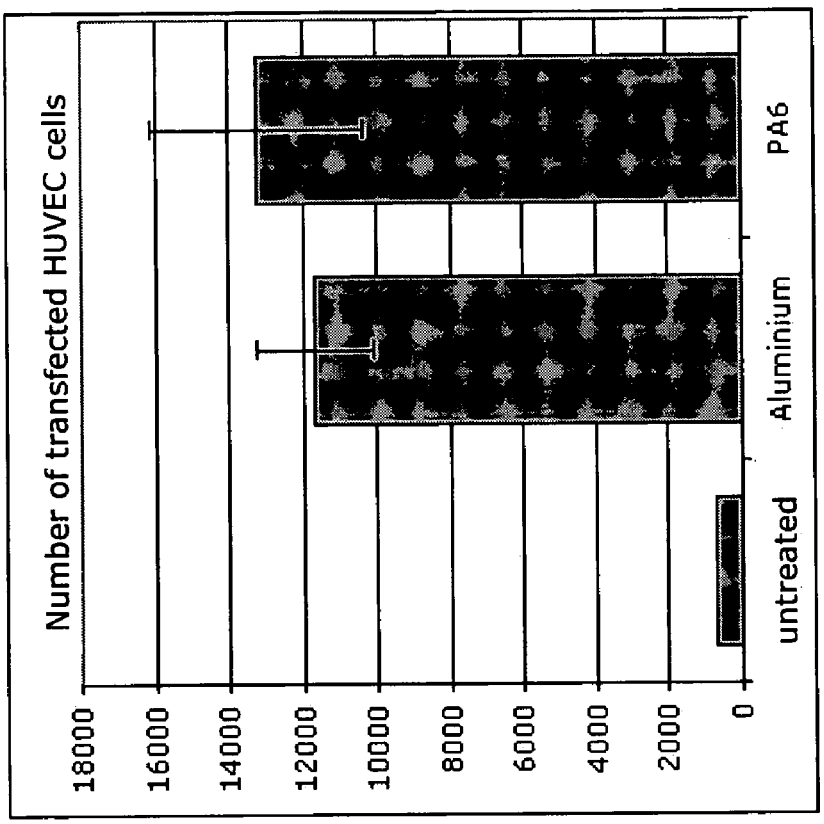
FIG. 16 shows diagrams of a flow-cytometric analysis of HUVEC cells (human endothelial cells) after electroporation using electrodes made of synthetic material according to the invention (PA6) compared to electrodes made of aluminium, a) number of dead cells stained with propidiumjodide, b) number of transfected living cells, untreated=respectively without application of a voltage pulse.
Figure 16:
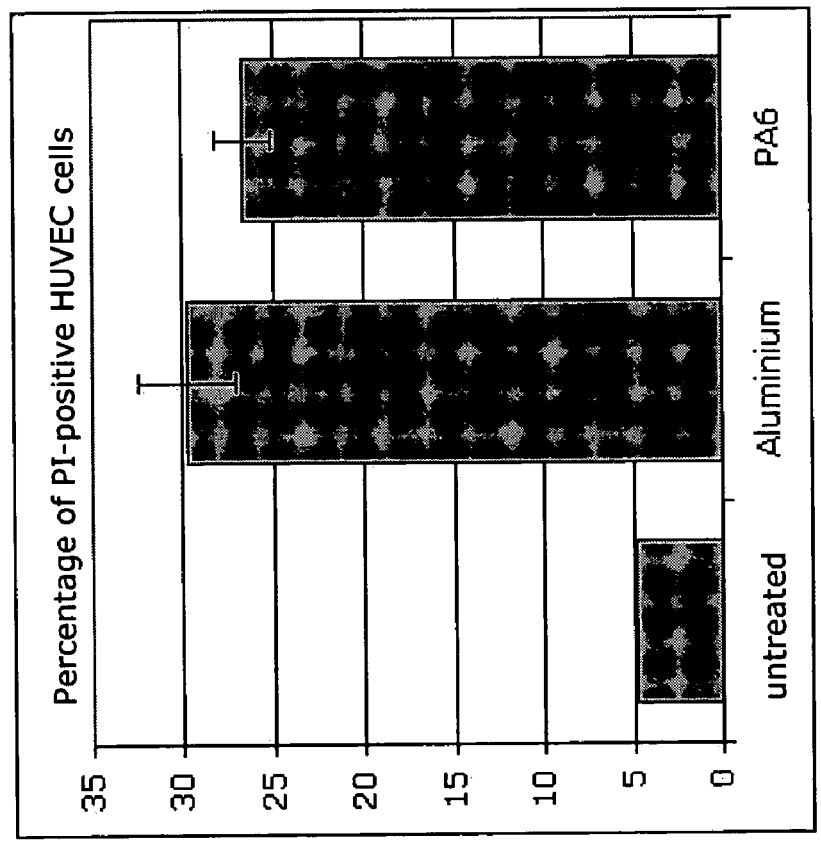

FIGS. 14 to 16 show diagrams of flow-cytometric analyses of transfected cells using cuvettes having electrodes according to the invention according to FIG. 13, which have a distance to each other of 1.5 mm. These containers are tested in direct comparison to cuvettes having electrodes made of aluminium with a distance between the electrodes of 2 mm. Due to the 25% reduction of the distance between the electrodes the higher resistance of the material of the doped plastic was compensated in respect of aluminium in order to achieve effectively the same conductivity per cross-sectional surface. The experimental procedure with polymer cuvettes corresponds to that with aluminium, wherein an electroporator having spring contacts made of brass (Nucleofector™ I, amaxa GmbH, Cologne) was used. Cell specific Nucleofector™ kits (amaxa GmbH, Cologne) were always used as solutions for receiving the cells. The cuvettes according to the invention always comprise electrodes consisting of polyamide (PA6 or PA66) doped with about 38-42% w/w carbon fibers and about 33-37% w/w graphite (overall concentration of the dope: about 70-80% w/w).

FIG. 14 shows diagrams of a flow-cytometric analysis of HL-60 cells (human lymphoma cells) after electroporation using polymer electrodes (PA6) according to the invention compared to electrodes made of aluminium. 2 µg pEGFP-C1 DNA (Clontech) were added to each probe of 100 µl solution including $10^6$ HL-60 cells (ATCC). Two voltage pulses (1000 V, 100 µs and $U_{start}$=90 V, 75 mC) were applied to various cuvettes containing these probes which were then immediately incubated in Iscove's modified Dulbecco's medium containing L-glutamine and 20% fetal calf serum (Gibco) in an incubator at 37° C./5% $CO_2$. After 24 hours the cells were harvested and propidiumjodide as well as 25.000 APC-marked beads (Becton Dickinson) were added to each probe. Determination of propidiumjodide-stained cells and transfected cells based on the absolute number of cells per probe in a flow-cytometer (FASCalibur, Becton Dickinson) was possible this way. It turned out herein that the transfection efficiency could be significantly increased and that the mortality rate could be slightly decreased by the use of cuvettes according to the invention in comparison to conventional cuvettes having electrodes made of aluminium.

FIG. 15 shows diagrams of a flow-cytometric analysis of $CD3^+$ T-cells after electroporation using polymer electrodes (PA6) according to the invention in comparison to electrodes made of aluminium. 2 µg pH-$2K^K$ (mouse MHC I heavy chain) were added to each probe of 100 µl solution containing $5 \times 10^6$ freshly isolated PBMC. Two voltage pulses (1000 V, 100 µs and $U_{start}$=96 V, 56 mC) were applied without interruption to various cuvettes containing these probes which are then directly incubated in AIM-V medium containing 10% fetal calf serum (Gibco) in an incubator at 37° C./5% $CO_2$. After 24 hours the cells were harvested and propidiumjodide as well as 25.000 APC-marked beads (Becton Dickinson) per probe were added. Additionally, the cells were stained using the fluorescein-isothiocyanate-stained anti-H-$2K^K$ antibody (Becton Dickinson) and an antibody against the human T-cell-specific CD3 antigen which is coupled to APC (Becton Dickinson). Determination of propidiumjodide-stained cells and transfected T-cells based on the absolute number of cells per probe in a flow-cytometer (FASCalibur, Becton Dickinson) was hereby possible. Approximately similar results could be achieved this way.

FIG. 16 shows diagrams of a flow-cytometric analysis of human umbilical cord vein endothelial cells (HUVEC) after electroporation using polymer electrodes (PA6) according to the invention in comparison to electrodes made of aluminium. 2 µg pEGFP-C1 DNA (Clontech) was added to each probe of 100 µl solution containing $6.8 \cdot 10^5$ HUVEC cells. A voltage pulse (1000 V, 100 µs) was applied to various cuvettes containing these probes which were then directly incubated in EGM-2 medium for endothelial cells (Clonetics) in an incubator at 37° C./5% $CO_2$. After 24 hours the cells were harvested and porpidiumjodide as well as 25.000 APC-marked beads (Becton Dickinson) were added to each probe. Determination of propidiumjodide-stained cells and transfected cells based on the absolute number of cells per probe in a flow-cytometer (FASCalibur, Becton Dickinson) was possible this way. It turned out herein that with the use of cuvettes according to the invention instead of conventional cuvettes having electrodes made of aluminium, the transfection efficiency could be increased and the mortality rate could be decreased.

Figure 17:
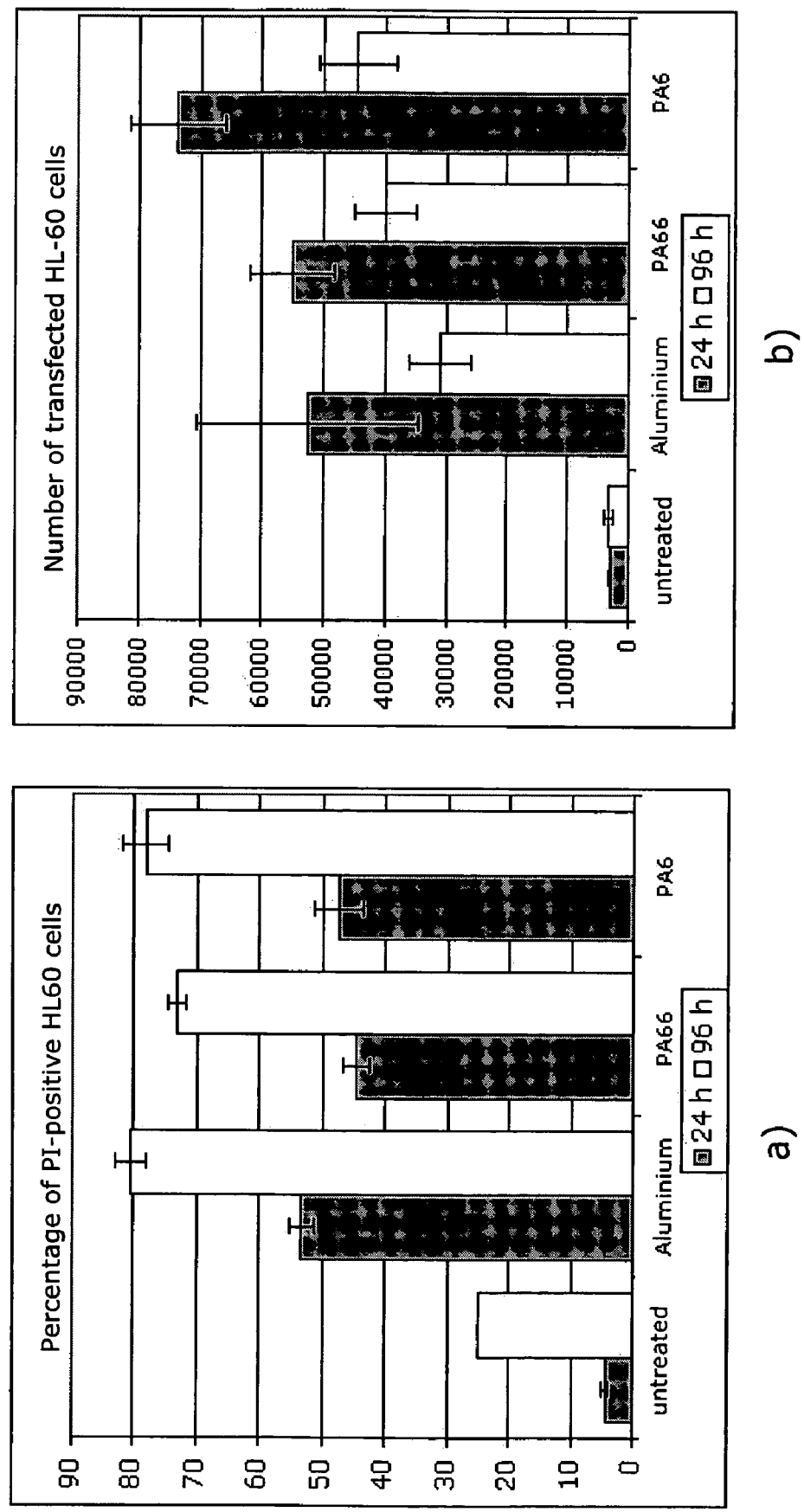
FIG. 17 shows diagrams of a flow-cytometric analysis of HL-60 cells (human lymphoma cells) 24 and 96 hours after electroporation using electrodes made of synthetic material according to the invention (PA66 and PA6) compared to electrodes made of aluminium, a) number of dead cells stained with propidiumjodide, b) number of transfected living cells, untreated=respectively without application of a voltage pulse.

FIG. 17 shows diagrams of a flow-cytometric analysis of HL-60 cells (human lymphoma cells) 24 and 96 hours after electroporation using polymer electrodes (PA66 and PA6) according to the invention in comparison to electrodes made of aluminium. Conditions and procedures generally correspond to those described in FIG. 14 with the exception that the cuvettes made of aluminium as well as the cuvettes according to the invention have a distance between the electrodes of 2 mm. The cuvettes used herein each further have electrodes made of polyamide doped with about 33-37% w/w carbon fibers and about 23-27% w/w graphite (overall concentration of the dope: about 55-65% w/w). In order to compensate the higher resistance of the polymer electrodes different pulse parameters are used herein (Synthetic material: 1000 V, 100 µs and $U_{start}$=102 V, 75 mC and Aluminium: 800 V, 100 µs and $U_{start}$=90 V, 75 mC). Also in this approach, the transfection efficiency could be slightly increased and the mortality rate could be slightly decreased by the use of polymer electrodes according to the invention.

LIST OF ABBREVIATIONS USED

A Ampere

C Coulomb

CHO Chinese hamster ovary cm Centimeter

DNA Deoxyribonucleic acid

Gew.-% Percent by weight h Hours

HL-60 Human lymphoma 60

HUVEC Human umbilical cord vein endothelial cells kV Kilovolt mC Millicoulomb mM Millimolar ms Milliseconds PA Polyamide PBMC Peripheral blood mononuclear cells PBS Phosphate-buffered saline pH Negative logarithm of the hydrogen-ion concentration PJ Propidiumjodide RNA Ribonucleic acid RPMI Rosewell Park Memorial Institute µg Microgram µl Microliter µs Microseconds U Voltage $U_{Anfang}$ Voltage$_{start}$ V Volt

LIST OF REFERENCE NUMBERS

1 Experimental assembly
2 Spacer plate
3 Electrode
4 Electrode
5 Recess
6 Copper plate
7 Copper plate
8 Threaded part
9 Threaded part
10 Inner space 11 Inner edges
12 Experimental assembly
13 Copper wire
14 Copper wire
20 Container
21 Outer limit
22 Inner chamber
23 Sidewall
24 Sidewall
25 Electrode
26 Electrode
27 Injection moulding channel
28 Injection moulding channel
30 Container
31 Outer limit
32 Inner chamber
33 Electrode
34 Electrode
35 Sidewall
36 Sidewall
37 Injection moulding channel
38 Injection moulding channel
39 Oblique part

The invention claimed is:

1. Container for receiving an aqueous solution, which comprises
at least one area which acts as an electrode when an electric voltage is applied and a subsequent discharge occurs,
wherein said at least one electrode is made of a conductive synthetic material which is, or is at least based on a plastic material which is doped with at least one conductive substance,
wherein an overall concentration of said dope in said plastic material is 20-80% w/w, and
wherein the container is for electroporation or electrofusion of cells, derivatives of cells, subcellular particles and/or vesicles and is, at least partially, formed by an outer limit which forms an inner chamber for receiving said solution.

2. Container according to claim 1, wherein said dope consists essentially of carbon fibers, graphite, soot and/or carbon nanotubes.

3. Container according to claim 1, wherein the overall concentration of said dope in said plastic material is 20-60% w/w.

4. Container according to claim 1, wherein the overall concentration of said dope in said plastic material is 40-80% w/w.

5. Container according to claim 1, wherein said plastic material is polycarbonate, polyetheretherketone, polypropylene, polyamide, polyphenylensulfide or a mixture of these polymers, or at least based on one or several of these polymers, and/or wherein said plastic material is an intrinsically conductive synthetic material.

6. Container according to claim 5, wherein said plastic material is an intrinsically conductive synthetic material and wherein said intrinsically conductive synthetic material is polyaniline, polyacetylene, poly-para-phenylene, poly-para-phenylensulfide, polypyrroles, polythiophene, polypropylene, or at least based on one or several of these polymers.

7. Container according to claim 1, wherein said outer limit is made of synthetic material.

8. Container according to claim 7, wherein said synthetic material is the same plastic material as the plastic material on which said at least one electrode is based.

9. Container according to claim 1, wherein said at least one electrode is integrated into said outer limit.

10. Container according to claim 1 comprising at least two electrodes being made of the same material.

11. Container according to claim 1 comprising at least two electrodes, wherein said at least two electrodes are made of different materials.

12. Container according to claim 1, wherein said at least one electrode is made of polyamide doped with 25-45% w/w carbon fibers and 15-35% w/w graphite.

13. Container according to claim 1, wherein said at least one electrode is made of polyamide doped with 30-50% w/w carbon fibers and 25-45% w/w graphite.

14. Container according to claim 1, wherein said at least one electrode is made of polycarbonate doped with 15-40% w/w carbon fibers and 1-40% w/w graphite.

15. Container according to claim 1, wherein said at least one electrode is made of polyetheretherketone doped with 30-50% w/w carbon fibers.

16. Container according to claim 1, wherein said at least one electrode is made of polyamide, preferably polyamide 66, doped with 20-40% w/w carbon fibers.

17. Container according to claim 1, wherein said at least one electrode is made of polypropylene doped with 20% w/w carbon fibers.

18. Container according to claim 1, wherein said at least one electrode is made of polyphenylensulfide doped with 30-50% w/w carbon fibers.

19. Container according to claim 1, wherein said outer limit comprises at least one opening for supplying said solution and at least one opening for draining off said solution.

20. Container arrangement comprising at least two, preferably 6, 12, 24, 48, 96 or more, containers according to claim 1 being joined to build one unit.

21. Container according to claim 1, wherein said aqueous solution comprises cells, derivatives of cells, subcellular particles and/or vesicles.

22. Container according to claim 7, wherein said synthetic material is a transparent plastic material.

23. Container according to claim 3, wherein the overall concentration of said dope in said plastic material is 40-60% w/w.

24. Container according to claim 3, wherein the overall concentration of said dope in said plastic material is 50-60% w/w.

25. Container according to claim 4, wherein the overall concentration of said dope in said plastic material is 50-80% w/w.

26. Container according to claim 4, wherein the overall concentration of said dope in said plastic material is 60-80% w/w.

27. Container according to claim 4, wherein the overall concentration of said dope in said plastic material is 70-80% w/w.

28. Container according to claim 12, wherein said at least one electrode is made of polyamide 66 or polyamide 6.

29. Container according to claim 12, wherein said at least one electrode is doped with 30-40% w/w-carbon fibers.

30. Container according to claim 12, wherein said at least one electrode is doped with 33-37% w/w carbon fibers.

31. Container according to claim 12, wherein said at least one electrode is doped with 20-30% w/w graphite.

32. Container according to claim 12, wherein said at least one electrode is doped with 23-27% w/w graphite.

33. Container according to claim 13, wherein said at least one electrode is made of polyamide 66 or polyamide 6.

34. Container according to claim 13, wherein said at least one electrode is doped with 35-45% w/w carbon fibers.

35. Container according to claim 13, wherein said at least one electrode is doped with 39-41% w/w carbon fibers.

36. Container according to claim 13, wherein said at least one electrode is doped with 30-40% w/w graphite.

37. Container according to claim 13, wherein said at least one electrode is doped with 34-36% w/w graphite.

38. Container according to claim 14, wherein at least one electrode is made of polycarbonate doped with 20% w/w carbon fibers and 15% w/w graphite.

39. Container according to claim 1, wherein said at least one electrode has a surface that is plane-parallel to a surface of a second electrode.

40. Container according to claim 1, wherein the electrode is moldable.

41. Container according to claim 40, wherein the electrode is injection-molded.

* * * * *